(12) United States Patent
Mueller et al.

(10) Patent No.: US 7,901,619 B2
(45) Date of Patent: Mar. 8, 2011

(54) SUSPENSION FOR REDUCING ODORS

(75) Inventors: Ulrich Mueller, Neustadt (DE); Michael Hesse, Worms (DE); Hermann Puetter, Neustadt (DE); Markus Schubert, Ludwigshafen (DE); Marcus Guzmann, Muehlhausen (DE); Juergen Huff, Ludwigshafen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 11/915,487

(22) PCT Filed: May 17, 2006

(86) PCT No.: PCT/EP2006/062376
§ 371 (c)(1),
(2), (4) Date: Nov. 26, 2007

(87) PCT Pub. No.: WO2006/125739
PCT Pub. Date: Nov. 30, 2006

(65) Prior Publication Data
US 2008/0206093 A1    Aug. 28, 2008

(30) Foreign Application Priority Data
May 24, 2005   (DE) .......................... 10 2005 023 857

(51) Int. Cl.
*A61L 9/00*    (2006.01)
(52) U.S. Cl. .................. 422/4; 422/5; 422/120
(58) Field of Classification Search .................. 422/4, 5, 422/120
See application file for complete search history.

(56) References Cited

U.S. PATENT DOCUMENTS

| 4,909,986 | A | * | 3/1990 | Kobayashi et al. ............... 422/4 |
| 5,648,508 | A | * | 7/1997 | Yaghi ................................. 556/9 |
| 5,942,217 | A | * | 8/1999 | Woo et al. ....................... 424/76.1 |

FOREIGN PATENT DOCUMENTS

| EP | 1 574 158 | 9/2005 |
| JP | 2003-070890 | 3/2003 |
| JP | 2004-008357 | 1/2004 |
| WO | 00 23119 | 4/2000 |
| WO | 03 102000 | 12/2003 |

OTHER PUBLICATIONS

Chae, et al., A route to high surface area, porosity and inclusion of large molecules in crystals, Letters to Nature, vol. 427, pp. 523-527, 2004.
O'Keeffe, et al., "Frameworks for Extended Solids: Geometrical Design Principles", Journal of Solid State Chemistry, vol. 152, pp. 3-20, 2000.
U.S. Appl. No. 12/594,604, filed Oct. 5, 2009, Stein, et al.
U.S. Appl. No. 12/597,616, filed Oct. 26, 2009, Schubert, et al.
U.S. Appl. No. 12/601,022, filed Nov. 20, 2009, Schubert, et al.

* cited by examiner

*Primary Examiner* — Sean E Conley
(74) *Attorney, Agent, or Firm* — Oblon, Spivak, McClelland, Maier & Neustadt, L.L.P.

(57) ABSTRACT

The present invention relates to suspensions for odor reduction comprising a porous metal-organic framework material in a liquid, and also atomizer and methods for odor reduction using the suspensions. The invention likewise relates to the use of the suspensions for odor reduction.

9 Claims, No Drawings

SUSPENSION FOR REDUCING ODORS

CROSS-REFERENCE TO RELATED APPLICATIONS

The present application is a 35 U.S.C. §371 National Stage patent application of International patent application PCT/EP06/062376, filed on May 17, 2006, which claims priority to German patent application DE 102005023857.2, filed on May 24, 2005.

The present invention relates to a suspension and also to methods and use of such a suspension for odor reduction.

Odors, in particular what are termed bad odors, are in particular a problem in daily life.

In particular in the case of what are termed bad odors, humans are adversely affected by perception via their sense of smell.

This can frequently be reduced or reversed by using odor-forming substances which are generally perceived as good-smelling by humans. By this means, the bad odor is to be suppressed.

Frequently, the odor perceived by humans is caused by odor substances which, independently of the subjective odor perception, are harmful for the human organism. In this case, the use of "good-smelling" substances does not decrease the problematic presence of substances harmful to health.

A further possibility is to eliminate the odor produced by odor substances by the odor substances being chemically decomposed, for example by enzymes.

An alternative possibility is to decrease odors by the odor-causing odor substances being sorbed to certain materials. These sorbents, usually diluted, can be brought to the desired point of action by atomizers.

One such sorbent known in the prior art is cyclodextrin.

A disadvantage of the prior art sorbents or solutions, or suspensions or emulsions in which the sorbents are present, is their sometimes low efficiency for reducing the undesired odor.

There is therefore a requirement to provide alternatives to the prior art solutions or suspensions, in particular for the atomization.

The object of the present invention is thus to provide alternative suspensions and also method for reducing odor, wherein the sorbent present in the suspension is to have improved properties compared with those of the prior art.

The object is achieved by a suspension for odor reduction comprising a porous metal-organic framework material in a liquid, the framework material comprising at least one, at least bidentate, organic compound bound by coordination to at least one metal ion.

The object is likewise achieved by a method for odor reduction comprising the step of contacting a gas comprising the odor, or an odor adhering to the surface of an article or to an organism with a suspension.

This is because it has been found that by using a porous metal-organic framework material as described above, an efficient reduction of odor can take place.

The singular and also the plural of the term "odor" is used synonymously in the context of the present invention. In this case the term odor is any sensation potentially perceivable by the human sense of smell which can be generated by one or more odor substances.

In this context the term "potentially" means that the odor substance or the odor substances which generate an odor, in the context of the present invention, need not be present at a concentration which makes possible perception via the human sense of smell. According to the invention, the mere presence of such an odor substance or such odor substances is thus sufficient.

Preferably, however, the odor substance or the odor substances are present at a concentration which is perceivable by the average human sense of smell.

The concentration of the framework material in the suspension is preferably in the range from 0.001 to 5% by weight, based on the total weight of the suspension. Further preferably, the concentration is in the range from 0.01 to 2.5% by weight, more preferably in the range from 0.1 to 1% by weight, in each case based on the total weight of the suspension.

In the case of the liquid required for production of the suspension, use can be made of any liquids, provided that this liquid is suitable for suspending the framework material without this being chemically decomposed by the liquid.

Suitable liquids are, for example, those which comprise alcohols or water. In particular, preference is given to water as liquid.

Further preference is given to liquids which enable easy atomization of the suspension formed together with the framework material.

By means of the atomization, a particularly preferred and efficient distribution of the suspension, in particular by fine droplet formation, can be achieved.

Accordingly, the present invention further relates to an atomizer comprising an inventive suspension.

In this case, commercially conventional atomizers can be used.

The inventive suspension can comprise further chemical substances. In this case, for example odor substances may be mentioned which cause an odor perceived as pleasant by humans. Such substances are frequently also termed fragrances or scents.

As already discussed above, the present invention also relates to a method for odor reduction. Advantageously, the reduction is performed to an extent so great that the odor-producing odor substance or the odor substances are no longer perceived by the average human sense of smell, i.e. the odor is removed.

The odor can be odors of daily life, or else comprise the most varied odors which can occur in the most varied applications. Those which may be mentioned by way of example are kitchen odor, sweat odor, incontinence odor, food odor, for example alcohol or fish odor, toilet odor, or odor which is caused by tobacco smoke, for example cigarette smoke.

It is known to those skilled in the art that the most varied odors can be reduced in the context of the present invention.

The odor can adhere to an organism. The organism can be a human or an animal, for example a dog or a cat. Contacting the organism with the suspension can be performed by the means that those or the affected body parts are uniformly rubbed with the suspension, or, the suspension is applied using an atomizer, for example. The inventive suspension can then be removed again, for example by washing.

Furthermore, the odor can adhere to the surface of an article. In this case, the terms "surface" and also "article" are to be interpreted very broadly. In the context of the present invention, in particular, adhesion to a surface of an article is always the case when the odor substances generating the odor, or the generating odor substance, can be brought into contact with the suspension.

Articles can be of the most varied nature and originate, for example, from daily life. those which may be mentioned here, by way of example, are woven fabrics and materials, for example clothes, upholstered furniture, curtains or blankets, furniture made of wood, plastic or another material, glass surfaces such as windows, wallpapers, walls and ceilings, floors, carpets or the like.

The affected surfaces can be moistened, for example using an inventive atomizer using the inventive suspension. To remove the suspension, this can be washed or wiped off. Also, under some circumstances, the suspension's remaining on the surface can be suitable.

In addition, it is possible first to apply the suspension to a suspension carrier which does not have adhering odor, or to impregnate this with the suspension and then to bring into contact with the inventive suspension the surface of an article with adhering odor, or the organism, using this carrier. Such a carrier can be, for example, a conventional cloth or the like. For the case of an odor-burdened gas such as air, likewise such a carrier can be used. Suitable items here are, for example, filters, as are used in a varied manner. For instance, kitchen odors can be reduced according to the invention, for example by filters present in steam exhaust hoods.

In addition, the odor reduction may likewise relate to a gas in which the odor substance or the odor substances which generate the odor are present.

In the context of the present invention, for simplicity the term "gas" is also used when this relates to gas mixtures, for example air. In the case of the relevant gases, it is merely necessary that these are in the gaseous state on contacting with the suspension.

Preferably, the gas has a boiling point or boiling range which is below room temperature. However, it is also possible that higher-boiling fluid systems are used if these are released, for example, as off-gases at elevated temperature and come into contact with the inventive suspension before their condensation.

Preferably, the gas is natural gas, biogas, off-gas, air, exhaust air or inert gas. More preference is given to natural gas, biogas, air and exhaust air. In particular preference is given to biogas, air and exhaust air. Very particular preference is given to air.

The gas can be present in open, or at least partially closed, systems. In particular in the case of natural gas and biogas, these can be pipes, pipelines, tank containers, transport containers or natural gas containers, as are used, for example, for storage in the ground or as tanks for motor vehicles. In the case of off-gases, these are preferably industrial off-gases or those off-gases as arise in combustion processes (for example in internal combustion engines). In addition, preferably the gas is indoor air in buildings or rooms as in living rooms and dining rooms, or in particular in kitchens. The internal air in means of locomotion such as automobiles, trucks, trains or ships may be mentioned here. Likewise, the internal air in appliances, for example dishwashing machines, may be mentioned.

In this case the gas which the odor substance or the odor substances which generate the odor can likewise be brought into contact by atomizing the suspension. In addition to the treatment of the gases themselves, the systems in contact with the gases, such as the surfaces of the inner walls of the above-mentioned pipes, pipelines, tank containers, transport containers or natural gas containers can also be brought into contact with the inventive suspension.

In particular in the cases in which the gas is natural gas, air, exhaust air or inert gas, the odor substance can originally be a constituent of a liquid (for example water or petroleum) or solid medium which then transfers into the phase of the gas situated above the liquid or solid surface and then is removed from this. For example, the gas can be a gas within packaging (ambient gas) of solid articles which in the course of time release odor substances within the package to the ambient gas. In this case the ambient gas is air or inert gas. A further example is that of polymers in which monomers which were not reacted in the production of the polymers, but are still remaining in the polymer and in the course of time are being released to the ambient gas, for example the internal air, and are the odor substances to be separated off. Likewise, further highly volatile components may be present in the polymer which can be released to the ambient gas. In this case, for example, initiators or stabilizers and other additives may be mentioned. A survey of such components is given in Plastics Additive Handbook, Hans Zweifel, Hanser Verlag, Munich (ISBN 3-446-21654-5). In this case also, alternatively or additionally to contacting the gas with the inventive suspension, the surface of the articles can be treated with the inventive suspension.

The odor substance or the odor substances which generate the odor can be present in the gas in dissolved form, or be themselves gaseous and thus be a "constituent" of a gas mixture. In the context of the present invention, the term "odor substance" is likewise used for simplification, even when it is a mixture of a plurality of odor substances. Odor substances in this case are substances which can be perceived via the human sense of smell.

Preferably, the odor substance is a volatile organic or inorganic compound which comprises at least one of the elements nitrogen, phosphorus, oxygen, sulfur, fluorine, chlorine, bromine or iodine, or is an unsaturated or aromatic hydrocarbon or a saturated or unsaturated aldehyde or ketone. More preferred elements are nitrogen, oxygen, phosphorus, sulfur, chlorine, bromine; in particular preference is given to nitrogen, oxygen, phosphorus and sulfur.

In particular, the odor substance is ammonia, hydrogen sulfide, sulfur oxides, nitrogen oxides, ozone, cyclic or acyclic amines, thiols, thioethers and also aldehydes, ketones, esters, ether acids or alcohols. Particular preference is given to ammonia, hydrogen sulfide, organic acids (preferably acetic acid, propionic acid, butyric acid, isobutyric acid, valeric acid, isovaleric acid, caproic acid, heptylic acid, lauric acid, perlargonic acid) and also cyclic or acyclic hydrocarbons which comprise nitrogen or sulfur, and also saturated or unsaturated aldehydes, such as hexanal, heptanal, octanal, nonanal, decanal, octenal or nonenal and, in particular, volatile aldehydes such as butyraldehyde, propionaldehyde, acetaldehyde and formaldehyde and furthermore power fuels such as gasoline, diesel (ingredients).

The odor substances can also be fragrances which are used, for example for producing perfumes. Fragrances or oils which release such fragrances which may be mentioned by way of example are: essential oils, basil oil, geranium oil, mint oil, cananga oil, cardamom oil, lavender oil, peppermint oil, muscat oil, camomile oil, eucalyptus oil, rosemary oil, lemon oil, lime oil, orange oil, bergamot oil, clary oil, coriander oil, cypress oil, 1,1-dimethoxy-2-pherylethane, 2,4-dimethyl-4-phenyltetrahydrofuran, dimethyltetrahydrobenzaldehyde, 2,6-dimethyl-7-octen-2-ol, 1,2-diethoxy-3,7-dimethyl-2,6-octadiene, phenylacetaldehyde, rose oxide, ethyl 2-methylpentanoate, 1-(2,6,6-trimethyl-1,3-cyclohexadien-1-yl)-2-buten-1-one, ethylvanillin, 2,6-dimethyl-2-octenol, 3,7-dimethyl-2-octenol, tert-butyl cyclohexylacetate, anisyl acetates, allyl cyclohexyloxyacetate, ethyllinalool, eugenol, coumarin, ethyl acetoacetate, 4-phenyl-2,4,6-trimethyl-1,3-dioxane, 4-methylene-3,5,6,6-tetramethyl-2-heptanone, ethyl tetrahydrosafranate, geranylnitrile, cis-3-hexen-1-ol, cis-3-hexenyl acetate, cis-3-hexenyl methyl carbonates, 2,6-dimethyl-5-hepten-1-al, 4-(tricyclo[5.2.1.0]decylidene)-8-butanal, 5-(2,2,3-trimethyl-3-cyclopentenyl)-3-methylpentan-2-ol, p-tert-butyl-alpha-methyl-hydrocimmaldehyde, ethyl [5.2.1.0] tricyclodecanecarboxylate, geraniol, citronellol, citral, linalool, linalyl acetate, ionones, phenylethanol or mixtures thereof.

In the context of the present invention, a volatile odor substance preferably has a boiling point or boiling range of below 300° C. More preferably, the odor substance is a highly volatile compound or mixture. In particular preferably, the odor substance has a boiling point or boiling range of below 250° C., more preferably below 230° C., in particular preferably below 200° C.

Preference is likewise given to odor substances which have a high volatility. The vapor pressure can be used as index of the volatility. In the context of the present invention, a volatile odor substance preferably has a vapor pressure of greater than 0.001 kPa (20° C.). More preferably, the odor substance is a highly volatile compound or mixture. In particular preferably, the odor substance has a vapor pressure of greater than 0.01 kPa (20° C.), more preferably a vapor pressure of greater than 0.05 kPa (20° C.). Particularly preferably, the odor substances have a vapor pressure of greater than 0.1 kPa (20° C.).

The porous metal-organic framework material which is present in the inventive suspension comprises at least one, at least bidentate, organic compound bound by coordination to at least one metal ion. This metal-organic framework material (MOF) is described, for example, in U.S. Pat. No. 5,648,508, EP-A-0 790 253, M. O-Keeffe et al., J. Sol. State Chem., 152 (2000), pages 3 to 20, H. Li et al., Nature 402, (1999), page 276, M. Eddaoudi et al., Topics in Catalysis 9, (1999), pages 105 to 111, B. Chen et al., Science 291, (2001), pages 1021 to 1023 and DE-A-101 11 230.

The MOFs according to the present invention comprise pores, in particular micropores and/or mesopores. Micropores are defined as those having a diameter of 2 nm or less and mesopores are defined by a diameter in the range from 2 to 50 nm, in each case in accordance with the definition as specified by Pure Applied Chem. 45, page 71, in particular on page 79 (1976). The presence of micropores and/or mesopores can be studied using sorption measurements, these measurements determining the MOF uptake capacity for nitrogen at 77 kelvin as specified in DIN 66131 and/or DIN 66134.

Preferably, the specific surface area, calculated according to the Langmuir model (DIN 66131, 66134) for an MOF in powder form is greater than 5 m$^2$/g, more preferably greater than 10 m$^2$/g, more preferably greater than 50 m$^2$/g, still more preferably greater than 500 m$^2$/g, still more preferably greater than 1000 m$^2$/g, and particularly preferably greater than 1500 m$^2$/g.

The metal component in the framework material according to the present invention is preferably selected from the groups Ia, IIa, IIIa, IVa to VIIIa and Ib to VIb. Particular preference is given to Mg, Ca, Sr, Ba, Sc, Y, Ti, Zr, Hf, V, Nb, Ta, Cr, Mo, W, Mn, Re, Fe, Ro, Os, Co, Rh, Ir, Ni, Pd, Pt, Cu, Ag, Au, Zn, Cd, Hg, Al, Ga, In, Tl, Si, Ge, Sn, Pb, As, Sb and Bi. More preference is given to Zn, Cu, Ni, Pd, Pt, Ru, Rh and Co. In particular preference is given to Zn, Al, Ni and Cu. With respect to the ions of these elements, those which may particularly be mentioned are $Mg^{2+}$, $Ca^{2+}$, $Sr^{2+}$, $Ba^{2+}$, $Sc^{3+}$, $Y^{3+}$, $Ti^{4+}$, $Zr^{4+}$, $Hf^{4+}$, $V^{4+}$, $V^{3+}$, $V^{2+}$, $Nb^{3+}$, $Ta^{3+}$, $Cr^{3+}$, $Mo^{3+}$, $W^{3+}$, $Mn^{3+}$, $Mn^{2+}$, $Re^{3+}$, $Re^{2+}$, $Fe^{3+}$, $Fe^{2+}$, $Ru^{3+}$, $Ru^{2+}$, $Os^{3+}$, $Os^{2+}$, $Co^{3+}$, $Co^{2+}$, $Rh^{2+}$, $Rh^+$, $Ir^{2+}$, $Ir^+$, $Ni^{2+}$, $Ni^+$, $Pd^{2+}$, $Pd^+$, $Pt^{2+}$, $Pt^+$, $Cu^{2+}$, $Cu^+$, $Ag^+$, $Au^+$, $Zn^{2+}$, $Cd^{2+}$, $Hg^{2+}$$Al^{3+}$, $Ga^{3+}$, $In^{3+}$, $Tl^{3+}$, $Si^{4+}$, $Si^{2+}$, $Ge^{4+}$, $Ge^{2+}$, $Sn^{4+}$, $Sn^{2+}$, $Pb^{4+}$, $Pb^{2+}$, $As^{5+}$, $As^{3+}$, $As^+$, $Sb^{5+}$, $Sb^{3+}$, $Sb^+$, $Bi^{5+}$, $Bi^{3+}$ and $Bi^+$.

The term "at least bidentate organic compound" designates an organic compound which comprises at least one functional group which is able to form, to a given metal ion, at least two, preferably three, coordinate bonds, and/or to two or more, preferably three metal atoms, in each case one coordinate bond.

As functional groups via which said coordinate bonds can be formed, in particular, for example the following functional groups may be mentioned: —$CO_2H$, —$CS_2H$, —$NO_2$, —$B(OH)_2$, —$SO_3H$, —$Si(OH)_3$, —$Ge(OH)_3$, —$Sn(OH)_3$, —$Si(SH)_4$, —$Ge(SH)_4$, —$Sn(SH)_3$, —$PO_3H$, —$AsO_3H$, —$AsO_4H$, —$P(SH)_3$, —$As(SH)_3$, —$CH(RSH)_2$, —$C(RSH)_3$, —$CH(RNH_2)_2$, —$C(RNH_2)_3$, —$CH(ROH)_2$, —$C(ROH)_3$, —$CH(RCN)_2$, —$C(RCN)_3$, where R, for example, is preferably an alkylene group having 1, 2, 3, 4 or 5 carbon atoms, for example a methylene, ethylene, n-propylene, i-propylene, n-butylene, i-butylene, tert-butylene or n-pentylene group. or an aryl group comprising 1 or 2 aromatic nuclei, for example 2 $C_6$ rings which, if appropriate, can be condensed and, independently of one another, can be suitably substituted by at least in each case one substituent, and/or which independently of one another, in each case, can comprise at least one heteroatom, for example N, O and/or S. According to likewise preferred embodiments, functional groups may be mentioned in which the abovementioned radical R is not present. In this respect, inter alia, —$CH(SH)_2$, —$C(SH)_3$, —$CH(NH_2)_2$, —$C(NH_2)_3$, —$CH(OH)_2$, —$C(OH)_3$, —$CH(CN)_2$ or —$C(CN)_3$ may be mentioned.

The at least two functional groups can in principle be bound to any suitable organic compound, provided that it is ensured that the organic compound having these functional groups is capable of forming the coordinate bond and for producing the framework material.

Preferably, the organic compounds which comprise the at least two functional groups are derived from a saturated or unsaturated aliphatic compound or an aromatic compound or a compound which is both aliphatic and aromatic.

The aliphatic compound or the aliphatic part of the both aliphatic and aromatic compound can be linear and/or branched and/or cyclic, a plurality of cycles also being possible per compound. Further preferably, the aliphatic compound or the aliphatic part of the both aliphatic and also aromatic compound comprises 1 to 15, further preferably 1 to 14, further preferably 1 to 13, further preferably 1 to 12, further preferably 1 to 11, and in particular preferably 1 to 10 carbon atoms, for example 1, 2, 3, 4, 5, 6, 7, 8, 9 or 10 carbon atoms. In particular preference is given here to inter alia methane, adamantine, acetylene, ethylene, or butadiene.

The aromatic compound or the aromatic part of the not only aromatic but also aliphatic compound can have one or else a plurality of nuclei, for example two, three, four or five nuclei, the nuclei being able to be present separately from one another and/or at least two nuclei being able to be present in condensed form. Particularly preferably, the aromatic compound, or the aromatic part of the not only aliphatic but also aromatic compound has one, two or three nuclei, one or two nuclei being particularly preferred. Independently of one another, in addition, each nucleus of said compound can comprise at least one heteroatom, for example N, O, S, B, P, Si, Al, preferably N, O and/or S. Further preferably, the aromatic compound, or the aromatic part of the not only aromatic but also aliphatic compound, comprises one or two $C_6$ nuclei, the two being present either separately from one another or in condensed form. In particular, as aromatic compounds, benzene, naphthalene and/or biphenyl and/or bipyridyl and/or pyridyl may be mentioned.

For example, inter alia, trans-muconic acid or fumaric acid or phenylenebisacrylic acids may be mentioned.

For example, in the context of the present invention, mention may be made of dicarboxylics acid, such as oxalic acid, succinic acid, tartaric acid, 1,4-butanedicarboxylic acid, 4-oxopyran-2,6-dicarboxylic acid, 1,6-hexanedicarboxylic acid, decanedicarboxylic acid, 1,8-heptadecanedicarboxylic acid, 1,9-heptadecanedicarboxylic acid, heptadecanedicarboxylic acid, acetylenedicarboxylic acid, 1,2-benzenedicarboxylic acid, 2,3-pyridinedicarboxylic acid, pyridine-2,3-dicarboxylic acid, 1,3-butadiene-1,4-dicarboxylic acid, 1,4-benzenedicarboxylic acid, p-benzenedicarboxylic acid, imidazole-2,4-dicarboxylic acid, 2-methylquinoline-3,4-dicarboxylic acid, quinoline-2,4-dicarboxylic acid, quinoxaline-2,3-dicarboxylic acid, 6-chloroquinoxaline-2,3-dicarboxylic acid, 4,4'-diaminophenylmethane-3,3'-dicarboxylic acid, quinoline-3,4-dicarboxylic acid, 7-chloro-4-hydroxyquinoline-2,8-dicarboxylic acid, diimidodicarboxylic acid, pyridine-2,6-dicarboxylic acid, 2-methylimidazole-4,5-dicarboxylic acid, thiophene-3,4-dicarboxylic acid, 2-isopropylimidazole-4,5-dicarboxylic acid, tetrahydropyran-4,4-dicarboxylic acid, perylene-3,9-dicarboxylic acid, perylenedicarboxylic acid, Pluriol E 200-dicarboxylic acid, 3,6-dioxaoctanedicarboxylic acid, 3,5-cyclohexadiene-1,2-dicarboxylic acid, octadicarboxylic acid, pentane-3,3-carboxylic acid, 4,4'-diamino-1,1'-diphenyl-3,3'-dicarboxylic acid, 4,4'-diaminodiphenyl-3,3'-dicarboxylic acid, benzidine-3,3'-dicarboxylic acid, 1,4-bis(phenylamino)benzene-2,5-dicarboxylic acid, 1,1'-dinaphthyl-S,S'-dicarboxylic acid, 7-chloro-8-methylquinoline-2,3-dicarboxylic acid, 1-anilinoanthraquinone-2,4'-dicarboxylic acid, polytetrahydrofuran-250-dicarboxylic acid, 1,4-bis(carboxymethyl)piperazine-2,3-dicarboxylic acid, 7-chloroquinoline-3,8-dicarboxylic acid, 1-(4-carboxy)phenyl-3-(4-chloro)phenylpyrazoline-4,5-dicarboxylic acid, 1,4,5,6,7,7-hexachloro-5-norbornene-2,3-dicarboxylic acid, phenylindanedicarboxylic acid, 1,3-dibenzyl-2-oxoimidazolidine-4,5-dicarboxylic acid, 1,4-cyclohexanedicarboxylic acid, naphthalene-1,8-dicarboxylic acid, 2-benzoylbenzene-1,3-dicarboxylic acid, 1,3-dibenzyl-2-oxoimidazolidine-4,5-cis-dicarboxylic acid, 2,2'-biquinoline-4,4'-dicarboxylic acid, pyridine-3,4-dicarboxylic acid, 3,6,9-trioxaundecanedicarboxylic acid, O-hydroxybenzophenonedicarboxylic acid, Pluriol E 300-dicarboxylic acid, Pluriol E 400-dicarboxylic acid, Pluriol E 600-dicarboxylic acid, pyrazole-3,4-dicarboxylic acid, 2,3-pyrazinedicarboxylic acid, 5,6-dimethyl-2,3-pyrazinedicarboxylic acid, 4,4'-diaminodiphenyletherdiimidodicarboxylic acid, 4,4'-diaminodiphenylmethanediimidodicarboxylic acid, 4,4'-diaminodiphenylsulfonediimidodicarboxylic acid, 2,6-naphthalenedicarboxylic acid, 1,3-adamantanedicarboxylic acid, 1,8-naphthalenedicarboxylic acid, 2,3-naphthalenedicarboxylic acid, 8-methoxy-2,3-naphthalenedicarboxylic acid, 8-nitro-2,3-naphthalenecarboxylic acid, 8-sulfo-2,3-naphthalenedicarboxylic acid, anthracene-2,3-dicarboxylic acid, 2',3'-diphenyl-p-terphenyl-4,4"-dicarboxylic acid, diphenyl-ether-4,4'-dicarboxylic acid, imidazole-4,5-dicarboxylic acid, 4(1 H)-oxothiochromene-2,8-dicarboxylic acid, 5-tert-butyl-1,3-benzenedicarboxylic acid, 7,8-quinolinedicarboxylic acid, 4,5-imidazoledicarboxylic acid, 4-cyclohexene-1,2-dicarboxylic acid, hexatriacontanedicarboxylic acid, tetradecanedicarboxylic acid, 1,7-heptadicarboxylic acid, 5-hydroxy-1,3-benzenedicarboxylic acid, pyrazine-2,3-dicarboxylic acid, furan-2,5-dicarboxylic acid, 1-nonene-6,9-dicarboxylic acid, eicosenedicarboxylic acid, 4,4'-dihydroxydiphenylmethane-3,3'-dicarboxylic acid, 1-amino-4-methyl-9,10-dioxo-9,10-dihydroanthracene-2,3-dicarboxylic acid, 2,5-pyridinedicarboxylic acid, cyclohexene-2,3-dicarboxylic acid, 2,9-dichlorofluororubin-4,11-dicarboxylic acid, 7-chloro-3-methylquinoline-6,8-dicarboxylic acid, 2,4-dichlorobenzophenone-2',5'-dicarboxylic acid, 1,3-benzenedicarboxylic acid, 2,6-pyridinedicarboxylic acid, 1-methylpyrrole-3,4-dicarboxylic acid, 1-benzyl-1H-pyrrole-3,4-dicarboxylic acid, anthraquinone-1,5-dicarboxylic acid, 3,5-pyrazoledicarboxylic acid, 2-nitrobenzene-1,4-dicarboxylic acid, heptane-1,7-dicarboxylic acid, cyclobutane-1,1-dicarboxylic acid 1,14-tetradecanedicarboxylic acid, 5,6-dehydronorbornane-2,3-dicarboxylic acid or 5-ethyl-2,3-pyridinedicarboxylic acid, tricarboxylic acids such as 2-hydroxy-1,2,3-propanetricarboxylic acid, 7-chloro-2,3,8-quinolinetricarboxylic acid, 1,2,4-benzenetricarboxylic acid, 1,2,4-butanetricarboxylic acid, 2-phosphono-1,2,4-butanetricarboxylic acid, 1,3,5-benzenetricarboxylic acid, 1-hydroxy-1,2,3-propanetricarboxylic acid, 4,5-dihydro-4,5-dioxo-1H-pyrrolo[2,3-F]quinoline-2,7,9-tricarboxylic acid, 5-acetyl-3-amino-6-methylbenzene-1,2,4-tricarboxylic acid, 3-amino-5-benzoyl-6-methylbenzene-1,2,4-tricarboxylic acid, 1,2,3-propanetricarboxylic acid or aurintricarboxylic acid, or tetracarboxylic acids such as 1,1-dioxidoperylo[1,12-BCD]thiophene-3,4,9,10-tetracarboxylic acid, perylenetetracarboxylic acids such as perylene-3,4,9,10-tetracarboxylic acid or perylene-1,12-sulfone-3,4,9,10-tetracarboxylic acid, butanetetracarboxylic acids such as 1,2,3,4-butanetetracarboxylic acid or meso-1,2,3,4-butanetetracarboxylic acid, decane-2,4,6,8-tetracarboxylic acid, 1,4,7,10,13,16-hexaoxacyclooctadecane-2,3,11,12-tetracarboxylic acid, 1,2,4,5-benzenetetracarboxylic acid, 1,2,11,12-dodecanetetracarboxylic acid, 1,2,5,6-hexanetetracarboxylic acid, 1,2,7,8-octanetetracarboxylic acid, 1,4,5,8-naphthalenetetracarboxylic acid, 1,2,9,10-decanetetracarboxylic acid, benzophenonetetracarboxylic acid, 3,3',4,4'-benzophenonetetracarboxylic acid, tetrahydrofurantetracarboxylic acid or cyclopentanetetracarboxylic acids such as cyclopentane-1,2,3,4-tetracarboxylic acid.

Very particularly preferably, use is made of optionally at least monosubstituted mono-, di-, tri-, tetranuclear or higher nuclear aromatic di-, tri- or tetracarboxylic acids, each of the nuclei being able to comprise at least one heteroatom, two or more nuclei being able to comprise identical or different heteroatoms. For example, preference is given to mononuclear dicarboxylic acids, mononuclear tricarboxylic acids, mononuclear tetracarboxylic acids, dinuclear dicarboxylic acids, dinuclear tricarboxylic acids, dinuclear tetracarboxylic acids, trinuclear dicarboxylic acids, trinuclear tricarboxylic acids, trinuclear tetracarboxylic acids, tetranuclear dicarboxylic acids, tetranuclear tricarboxylic acids and/or tetranuclear tetracarboxylic acids. Suitable heteroatoms are, for example N, O, S, B, P, Si, Al, preferred heteroatoms in this case are N, S and/or O. Suitable substituents which may be mentioned in this respect is, inter alia, —OH, a nitro group, an amino group or an alkyl or alkoxy group.

In particular preferably, as at least bidentate organic compounds, use is made of acetylenedicarboxylic acid (ADC), benzenedicarboxylic acids, naphthalenedicarboxylic acids, biphenyldicarboxylic acids, for example 4,4'-biphenyldicarboxylic acid (BPDC), bipyridinedicarboxylic acids, for example 2,2'-bipyridinedicarboxylic acids, for example 2,2'-bipyridine-5,5'-dicarboxylic acid, benzenetricarboxylic acids, for example 1,2,3-benzenetricarboxylic acid or 1,3,5-benzenetricarboxylic acid (BTC), adamantanetetracarboxylic acid (ATC), adamantanedibenzoate (ADB), benzenetribenzoate (BTB), methanetetrabenzoate (MTB), adamantanetetrabenzoate, or dihydroxyterephthalic acids, for example 2,5-dihydroxyterephthalic acid (DHBDC).

Very particularly preferably, use is made of, inter alia, isophthalic acid, terephthalic acid, 2,5-dihydroxyterephthalic acid, 1,2,3-benzentricarboxylic acid, 1,3,5-benzenetricarboxylic acid, or 2,2'-bipyridine-5,5'-dicarboxylic acid.

In addition to these at least bidentate organic compounds, the MOF can also comprise one or more monodentate ligands.

Suitable solvent for producing the MOFs are, inter alia, ethanol, dimethylformamide, toluene, methanol, chlorobenzene, diethylformamide, dimethyl sulfoxide, water, hydrogen peroxide, methylamine, sodium hydroxide solution, N-methylpolidone ether, acetonitrile, benzyl chloride, triethylamine, ethylene glycol and mixtures thereof. Further metal ions, at least bidentate organic compounds and solvents for producing MOFs are described, inter alia, in U.S. Pat. No. 5,648,508 or DE-A 101 11 230.

The pore size of the MOF can be controlled by selection of the suitable ligand and/or of the at least bidentate organic compound. It is generally true that the greater the organic compound, the greater is the pore size. Preferably, the pore size is 0.2 nm to 30 nm, particularly preferably the pore size is in the range from 0.3 nm to 3 nm, based on the crystalline material.

Examples of MOFs are given hereinafter. In addition to the designation of the MOF, the metal and also the at least bidentate ligand, in addition the solvent and also the cell parameters (angle $\alpha$, $\beta$ and $\gamma$ and also the distances A, B and C in Å) are given. The latter were determined by X-ray diffraction.

| MOF-n | Ingredients molar ratio M + L | Solvent S | $\alpha$ | $\beta$ | $\gamma$ | a | b | c | Space group |
|---|---|---|---|---|---|---|---|---|---|
| MOF-0 | $Zn(NO_3)_2 \cdot 6H_2O$ $H_3(BTC)$ | Ethanol | 90 | 90 | 120 | 16.711 | 16.711 | 14.189 | P6(3)/Mcm |
| MOF-2 | $Zn(NO_3)_2 \cdot 6H_2O$ (0.246 mmol) $H_2(BDC)$ 0.241 mmol) | DMF Toluene | 90 | 102.8 | 90 | 6.718 | 15.49 | 12.43 | P2(1)/n |
| MOF-3 | $Zn(NO_3)_2 \cdot 6H_2O$ (1.89 mmol) $H_2(BDC)$ (1.93 mmol) | DMF MeOH | 99.72 | 111.11 | 108.4 | 9.726 | 9.911 | 10.45 | P-1 |
| MOF-4 | $Zn(NO_3)_2 \cdot 6H_2O$ (1.00 mmol) $H_3(BTC)$ (0.5 mmol) | Ethanol | 90 | 90 | 90 | 14.728 | 14.728 | 14.728 | P2(1)3 |
| MOF-5 | $Zn(NO_3)_2 \cdot 6H_2O$ (2.22 mmol) $H_2(BDC)$ (2.17 mmol) | DMF Chlorobenzene | 90 | 90 | 90 | 25.669 | 25.669 | 25.669 | Fm-3m |
| MOF-38 | $Zn(NO_3)_2 \cdot 6H_2O$ (0.27 mmol) $H_3(BTC)$ (0.15 mmol) | DMF Chlorobenzene | 90 | 90 | 90 | 20.657 | 20.657 | 17.84 | I4cm |
| MOF-31 $Zn(ADC)_2$ | $Zn(NO_3)_2 \cdot 6H_2O$ 0.4 mmol $H_2(ADC)$ 0.8 mmol | Ethanol | 90 | 90 | 90 | 10.821 | 10.821 | 10.821 | Pn(-3)m |
| MOF-12 $Zn_2(ATC)$ | $Zn(NO_3)_2 \cdot 6H_2O$ 0.3 mmol $H_4(ATC)$ 0.15 mmol | Ethanol | 90 | 90 | 90 | 15.745 | 16.907 | 18.167 | Pbca |
| MOF-20 ZnNDC | $Zn(NO_3)_2 \cdot 6H_2O$ 0.37 mmol $H_2NDC$ 0.36 mmol | DMF Chlorobenzene | 90 | 92.13 | 90 | 8.13 | 16.444 | 12.807 | P2(1)/c |
| MOF-37 | $Zn(NO_3)_2 \cdot 6H_2O$ 0.2 mmol $H_2NDC$ 0.2 mmol | DEF Chlorobenzene | 72.38 | 83.16 | 84.33 | 9.952 | 11.576 | 15.556 | P-1 |
| MOF-8 $Tb_2(ADC)$ | $Tb(NO_3)_3 \cdot 5H_2O$ 0.10 mmol $H_2ADC$ 0.20 mmol | DMSO MeOH | 90 | 115.7 | 90 | 19.83 | 9.822 | 19.183 | C2/c |
| MOF-9 $Tb_2(ADC)$ | $Tb(NO_3)_3 \cdot 5H_2O$ 0.08 mmol $H_2ADB$ 0.12 mmol | DMSO | 90 | 102.09 | 90 | 27.056 | 16.795 | 28.139 | C2/c |
| MOF-6 | $Tb(NO_3)_3 \cdot 5H_2O$ 0.30 mmol $H_2(BDC)$ 0.30 mmol | DMF MeOH | 90 | 91.28 | 90 | 17.599 | 19.996 | 10.545 | P21/c |
| MOF-7 | $Tb(NO_3)_3 \cdot 5H_2O$ 0.15 mmol $H_2(BDC)$ 0.15 mmol | $H_2O$ | 102.3 | 91.12 | 101.5 | 6.142 | 10.069 | 10.096 | P-1 |

-continued

| MOF-n | Ingredients molar ratio M + L | Solvent S | α | β | γ | a | b | c | Space group |
|---|---|---|---|---|---|---|---|---|---|
| MOF-69A | Zn(NO$_3$)$_2$•6H$_2$O 0.083 mmol 4,4'BPDC 0.041 mmol | DEF H$_2$O$_2$ MeNH$_2$ | 90 | 111.6 | 90 | 23.12 | 20.92 | 12 | C2/c |
| MOF-69B | Zn(NO$_3$)$_2$•6H$_2$O 0.083 mmol 2,6-NCD 0.041 mmol | DEF H$_2$O$_2$ MeNH$_2$ | 90 | 95.3 | 90 | 20.17 | 18.55 | 12.16 | C2/c |
| MOF-11 Cu$_2$(ATC) | Cu(NO$_3$)$_2$•2.5H$_2$O 0.47 mmol H$_2$ATC 0.22 mmol | H$_2$O | 90 | 93.86 | 90 | 12.987 | 11.22 | 11.336 | C2/c |
| MOF-11 Cu$_2$(ATC) dehydr. | | | 90 | 90 | 90 | 8.4671 | 8.4671 | 14.44 | P42/mmc |
| MOF-14 Cu$_3$(BTB) | Cu(NO$_3$)$_2$•2.5H$_2$O 0.28 mmol H$_3$BTB 0.052 mmol | H$_2$O DMF EtOH | 90 | 90 | 90 | 26.946 | 26.946 | 26.946 | Im-3 |
| MOF-32 Cd(ATC) | Cd(NO$_3$)$_2$•4H$_2$O 0.24 mmol H$_4$ATC 0.10 mmol | H$_2$O NaOH | 90 | 90 | 90 | 13.468 | 13.468 | 13.468 | P(-4)3m |
| MOF-33 Zn$_2$(ATB) | ZnCl$_2$ 0.15 mmol H$_4$ATB 0.02 mmol | H$_2$O DMF EtOH | 90 | 90 | 90 | 19.561 | 15.255 | 23.404 | Imma |
| MOF-34 Ni(ATC) | Ni(NO$_3$)$_2$•6H$_2$O 0.24 mmol H$_4$ATC 0.10 mmol | H$_2$O NaOH | 90 | 90 | 90 | 10.066 | 11.163 | 19.201 | P2$_1$2$_1$2$_1$ |
| MOF-36 Zn$_2$(MTB) | Zn(NO$_3$)$_2$•4H$_2$O 0.20 mmol H$_4$MTB 0.04 mmol | H$_2$O DMF | 90 | 90 | 90 | 15.745 | 16.907 | 18.167 | Pbca |
| MOF-39 Zn$_3$O(HBTB) | Zn(NO$_3$)$_2$4H$_2$O 0.27 mmol H$_3$BTB 0.07 mmol | H$_2$O DMF EtOH | 90 | 90 | 90 | 17.158 | 21.591 | 25.308 | Pnma |
| NO305 | FeCl$_2$•4H$_2$O 5.03 mmol formic acid 86.90 mmol | DMF | 90 | 90 | 120 | 8.2692 | 8.2692 | 63.566 | R-3c |
| NO306A | FeCl$_2$•4H$_2$O 5.03 mmol formic acid 86.90 mmol | DEF | 90 | 90 | 90 | 9.9364 | 18.374 | 18.374 | Pbcn |
| NO29 MOF-0 similar | Mn(Ac)$_2$•4H$_2$O 0.46 mmol H$_3$BTC 0.69 mmol | DMF | 120 | 90 | 90 | 14.16 | 33.521 | 33.521 | P-1 |
| BPR48 A2 | Zn(NO$_3$)$_2$6H$_2$O 0.012 mmol H$_2$BDC 0.012 mmol | DMSO Toluene | 90 | 90 | 90 | 14.5 | 17.04 | 18.02 | Pbca |
| BPR69 B1 | Cd(NO$_3$)$_2$4H$_2$O 0.0212 mmol H$_2$BDC 0.0428 mmol | DMSO | 90 | 98.76 | 90 | 14.16 | 15.72 | 17.66 | Cc |
| BPR92 A2 | Co(NO$_3$)$_2$•6H$_2$O 0.018 mmol H$_2$BDC 0.018 mmol | NMP | 106.3 | 107.63 | 107.2 | 7.5308 | 10.942 | 11.025 | P1 |
| BPR95 C5 | Cd(NO$_3$)$_2$4H$_2$O 0.012 mmol H$_2$BDC 0.36 mmol | NMP | 90 | 112.8 | 90 | 14.460 | 11.085 | 15.829 | P2(1)/n |
| CuC$_6$H$_4$O$_6$ | Cu(NO$_3$)$_2$•2.5H$_2$O 0.370 mmol H$_2$BDC(OH)$_2$ 0.37 mmol | DMF Chloro-benzene | 90 | 105.29 | 90 | 15.259 | 14.816 | 14.13 | P2(1)/c |
| M(BTC) MOF-0 like | Co(SO$_4$)H$_2$O 0.055 mmol H$_3$BTC 0.037 mmol | DMF | | as for MOF-0 | | | | | |

-continued

| MOF-n | Ingredients molar ratio M + L | Solvent S | α | β | γ | a | b | c | Space group |
|---|---|---|---|---|---|---|---|---|---|
| Tb($C_6H_4O_6$) | Tb($NO_3$)$_3$·5$H_2O$ 0.370 mmol $H_2$($C_6H_4O_6$) 0.56 mmol | DMF Chlorobenzene | 104.6 | 107.9 | 97.147 | 10.491 | 10.981 | 12.541 | P-1 |
| Zn($C_2O_4$) | $ZnCl_2$ 0.370 mmol oxalic acid 0.37 mmol | DMF Chlorobenzene | 90 | 120 | 90 | 9.4168 | 9.4168 | 8.464 | P(-3)1m |
| Co(CHO) | Co($NO_3$)$_2$·5$H_2O$ 0.043 mmol formic acid 1.60 mmol | DMF | 90 | 91.32 | 90 | 11.328 | 10.049 | 14.854 | P2(1)/n |
| Cd(CHO) | Cd($NO_3$)$_2$·4$H_2O$ 0.185 mmol formic acid 0.185 mmol | DMF | 90 | 120 | 90 | 8.5168 | 8.5168 | 22.674 | R-3c |
| Cu($C_3H_2O_4$) | Cu($NO_3$)$_2$·2.5$H_2O$ 0.043 mmol malonic acid 0.192 mmol | DMF | 90 | 90 | 90 | 8.366 | 8.366 | 11.919 | P43 |
| $Zn_6$(NDC)$_5$ MOF-48 | Zn($NO_3$)$_2$·6$H_2O$ 0.097 mmol 14NDC 0.069 mmol | DMF Chlorobenzene $H_2O_2$ | 90 | 95.902 | 90 | 19.504 | 16.482 | 14.64 | C2/m |
| MOF-47 | Zn($NO_3$)$_2$6$H_2O$ 0.185 mmol $H_2$(BDC[$CH_3$]$_4$) 0.185 mmol | DMF Chlorobenzene $H_2O_2$ | 90 | 92.55 | 90 | 11.303 | 16.029 | 17.535 | P2(1)/c |
| MO25 | Cu($NO_3$)$_2$·2.5$H_2O$ 0.084 mmol BPhDC 0.085 mmol | DMF | 90 | 112.0 | 90 | 23.880 | 16.834 | 18.389 | P2(1)/c |
| Cu-Thio | Cu($NO_3$)$_2$·2.5$H_2O$ 0.084 mmol thiophene dicarboxylic acid 0.085 mmol | DEF | 90 | 113.6 | 90 | 15.4747 | 14.514 | 14.032 | P2(1)/c |
| CIBDC1 | Cu($NO_3$)$_2$·2.5$H_2O$ 0.0084 mmol $H_2$(BDC$Cl_2$) 0.085 mmol | DMF | 90 | 105.6 | 90 | 14.911 | 15.622 | 18.413 | C2/c |
| MOF-101 | Cu($NO_3$)$_2$·2.5$H_2O$ 0.084 mmol BrBDC 0.085 mmol | DMF | 90 | 90 | 90 | 21.607 | 20.607 | 20.073 | Fm3m |
| $Zn_3$(BTC)$_2$ | $ZnCl_2$ 0.033 mmol $H_3$BTC 0.033 mmol | DMF EtOH Base Added | 90 | 90 | 90 | 26.572 | 26.572 | 26.572 | Fm-3m |
| MOF-j | Co($CH_3CO_2$)$_2$·4$H_2O$ (1.65 mmol) $H_3$(BZC) (0.95 mmol) | $H_2O$ | 90 | 112.0 | 90 | 17.482 | 12.963 | 6.559 | C2 |
| MOF-n | Zn($NO_3$)$_2$·6$H_2O$ $H_3$(BTC) | Ethanol | 90 | 90 | 120 | 16.711 | 16.711 | 14.189 | P6(3)/mcm |
| PbBDC | Pb($NO_3$)$_2$ (0.181 mmol) $H_2$(BDC) (0.181 mmol) | DMF Ethanol | 90 | 102.7 | 90 | 8.3639 | 17.991 | 9.9617 | P2(1)/n |
| Znhex | Zn($NO_3$)$_2$·6$H_2O$ (0.171 mmol) $H_3$BTB (0.114 mmol) | DMF p-Xylene Ethanol | 90 | 90 | 120 | 37.1165 | 37.117 | 30.019 | P3(1)c |
| AS16 | $FeBr_2$ 0.927 mmol $H_2$(BDC) 0.927 mmol | DMF anhydr. | 90 | 90.13 | 90 | 7.2595 | 8.7894 | 19.484 | P2(1)c |
| AS27-2 | $FeBr_2$ 0.927 mmol $H_3$(BDC) 0.464 mmol | DMF anhydr. | 90 | 90 | 90 | 26.735 | 26.735 | 26.735 | Fm3m |
| AS32 | $FeCl_3$ 1.23 mmol $H_2$(BDC) 1.23 mmol | DMF anhydr. Ethanol | 90 | 90 | 120 | 12.535 | 12.535 | 18.479 | P6(2)c |

| MOF-n | Ingredients molar ratio M + L | Solvent S | α | β | γ | a | b | c | Space group |
|---|---|---|---|---|---|---|---|---|---|
| AS54-3 | FeBr$_2$ 0.927 BPDC 0.927 mmol | DMF anhydr. n-Propanol | 90 | 109.98 | 90 | 12.019 | 15.286 | 14.399 | C2 |
| AS61-4 | FeBr$_2$ 0.927 mmol m-BDC 0.927 mmol | Pyridine anhydr. | 90 | 90 | 120 | 13.017 | 13.017 | 14.896 | P6(2)c |
| AS68-7 | FeBr$_2$ 0.927 mmol m-BDC 1.204 mmol | DMF anhydr. Pyridine | 90 | 90 | 90 | 18.3407 | 10.036 | 18.039 | Pca2$_1$ |
| Zn(ADC) | Zn(NO$_3$)$_2$·6H$_2$O 0.37 mmol H$_2$(ADC) 0.36 mmol | DMF Chlorobenzene | 90 | 99.85 | 90 | 16.764 | 9.349 | 9.635 | C2/c |
| MOF-12 Zn$_2$(ATC) | Zn(NO$_3$)$_2$·6H$_2$O 0.30 mmol H$_4$(ATC) 0.15 mmol | Ethanol | 90 | 90 | 90 | 15.745 | 16.907 | 18.167 | Pbca |
| MOF-20 ZnNDC | Zn(NO$_3$)$_2$·6H$_2$O 0.37 mmol H$_2$NDC 0.36 mmol | DMF Chlorobenzene | 90 | 92.13 | 90 | 8.13 | 16.444 | 12.807 | P2(1)/c |
| MOF-37 | Zn(NO$_3$)$_2$·6H$_2$O 0.20 mmol H$_2$NDC 0.20 mmol | DEF Chlorobenzene | 72.38 | 83.16 | 84.33 | 9.952 | 11.576 | 15.556 | P-1 |
| Zn(NDC) (DMSO) | Zn(NO$_3$)$_2$·6H$_2$O H$_2$NDC | DMSO | 68.08 | 75.33 | 88.31 | 8.631 | 10.207 | 13.114 | P-1 |
| Zn(NDC) | Zn(NO$_3$)$_2$·6H$_2$O H$_2$NDC | | 90 | 99.2 | 90 | 19.289 | 17.628 | 15.052 | C2/c |
| Zn(HPDC) | Zn(NO$_3$)$_2$·4H$_2$O 0.23 mmol H$_2$(HPDC) 0.05 mmol | DMF H$_2$O | 107.9 | 105.06 | 94.4 | 8.326 | 12.085 | 13.767 | P-1 |
| Co(HPDC) | Co(NO$_3$)$_2$·6H$_2$O 0.21 mmol H$_2$(HPDC) 0.06 mmol | DMF H$_2$O/Ethanol | 90 | 97.69 | 90 | 29.677 | 9.63 | 7.981 | C2/c |
| Zn$_3$(PDC)2.5 | Zn(NO$_3$)$_2$·4H$_2$O 0.17 mmol H$_2$(HPDC) 0.05 mmol | DMF/ClBz H$_2$0/TEA | 79.34 | 80.8 | 85.83 | 8.564 | 14.046 | 26.428 | P-1 |
| Cd$_2$(TPDC)2 | Cd(NO$_3$)$_2$·4H$_2$O 0.06 mmol H$_2$(HPDC) 0.06 mmol | Methanol/ CHP H$_2$O | 70.59 | 72.75 | 87.14 | 10.102 | 14.412 | 14.964 | P-1 |
| Tb(PDC)1.5 | Tb(NO$_3$)$_3$·5H$_2$O 0.21 mmol H$_2$(PDC) 0.034 mmol | DMF H$_2$O/Ethanol | 109.8 | 103.61 | 100.14 | 9.829 | 12.11 | 14.628 | P-1 |
| ZnDBP | Zn(NO$_3$)$_2$·6H$_2$O 0.05 mmol dibenzyl phosphate 0.10 mmol | MeOH | 90 | 93.67 | 90 | 9.254 | 10.762 | 27.93 | P2/n |
| Zn$_3$(BPDC) | ZnBr$_2$ 0.021 mmol 4,4'BPDC 0.005 mmol | DMF | 90 | 102.76 | 90 | 11.49 | 14.79 | 19.18 | P21/n |
| CdBDC | Cd(NO$_3$)$_2$·4H$_2$O 0.100 mmol H$_2$(BDC) 0.401 mmol | DMF Na$_2$SiO$_3$ (aq) | 90 | 95.85 | 90 | 11.2 | 11.11 | 16.71 | P21/n |
| Cd-mBDC | Cd(NO$_3$)$_2$·4H$_2$O 0.009 mmol H$_2$(mBDC) 0.018 mmol | DMF MeNH$_2$ | 90 | 101.1 | 90 | 13.69 | 18.25 | 14.91 | C2/c |
| Zn$_4$OBNDC | Zn(NO$_3$)$_2$·6H$_2$O 0.041 mmol BNDC | DEF MeNH$_2$ H$_2$O$_2$ | 90 | 90 | 90 | 22.35 | 26.05 | 59.56 | Fmmm |
| Eu(TCA) | Eu(NO$_3$)$_3$·6H$_2$O 0.14 mmol TCA 0.026 mmol | DMF Chlorobenzene | 90 | 90 | 90 | 23.325 | 23.325 | 23.325 | Pm-3n |

-continued

| MOF-n | Ingredients molar ratio M + L | Solvent S | α | β | γ | a | b | c | Space group |
|---|---|---|---|---|---|---|---|---|---|
| Tb(TCA) | Tb(NO$_3$)$_3$•6H$_2$O 0.069 mmol TCA 0.026 mmol | DMF Chlorobenzene | 90 | 90 | 90 | 23.272 | 23.272 | 23.372 | Pm-3n |
| Formates | Ce(NO$_3$)$_3$•6H$_2$O 0.138 mmol formic acid 0.43 mmol | H$_2$O Ethanol | 90 | 90 | 120 | 10.668 | 10.667 | 4.107 | R-3m |
|  | FeCl$_2$•4H$_2$O 5.03 mmol formic acid 86.90 mmol | DMF | 90 | 90 | 120 | 8.2692 | 8.2692 | 63.566 | R-3c |
|  | FeCl$_2$•4H$_2$O 5.03 mmol formic acid 86.90 mmol | DEF | 90 | 90 | 90 | 9.9364 | 18.374 | 18.374 | Pbcn |
|  | FeCl$_2$•4H$_2$O 5.03 mmol formic acid 86.90 mmol | DEF | 90 | 90 | 90 | 8.335 | 8.335 | 13.34 | P-31c |
| NO330 | FeCl$_2$•4H$_2$O 0.50 mmol formic acid 8.69 mmol | Formamide | 90 | 90 | 90 | 8.7749 | 11.655 | 8.3297 | Pnna |
| NO332 | FeCl$_2$•4H$_2$O 0.50 mmol formic acid 8.69 mmol | DIP | 90 | 90 | 90 | 10.0313 | 18.808 | 18.355 | Pbcn |
| NO333 | FeCl$_2$•4H$_2$O 0.50 mmol formic acid 8.69 mmol | DBF | 90 | 90 | 90 | 45.2754 | 23.861 | 12.441 | Cmcm |
| NO335 | FeCl$_2$•4H$_2$O 0.50 mmol formic acid 8.69 mmol | CHF | 90 | 91.372 | 90 | 11.5964 | 10.187 | 14.945 | P21/n |
| NO336 | FeCl$_2$•4H$_2$O 0.50 mmol formic acid 8.69 mmol | MFA | 90 | 90 | 90 | 11.7945 | 48.843 | 8.4136 | Pbcm |
| NO13 | Mn(Ac)$_2$•4H$_2$O 0.46 mmol benzoic acid 0.92 mmol bipyridine 0.46 mmol | Ethanol | 90 | 90 | 90 | 18.66 | 11.762 | 9.418 | Pbcn |
| NO29 MOF-0 like | Mn(Ac)$_2$•4H$_2$O 0.46 mmol H$_3$BTC 0.69 mmol | DMF | 120 | 90 | 90 | 14.16 | 33.521 | 33.521 | P-1 |
| Mn(hfac)$_2$ (O$_2$CC$_6$H$_5$) | Mn(Ac)$_2$•4H$_2$O 0.46 mmol Hfac 0.92 mmol bipyridine 0.46 mmol | Ether | 90 | 95.32 | 90 | 9.572 | 17.162 | 14.041 | C2/c |
| BPR43G2 | Zn(NO$_3$)$_2$•6H$_2$O 0.0288 mmol H$_2$BDC 0.0072 mmol | DMF CH$_3$CN | 90 | 91.37 | 90 | 17.96 | 6.38 | 7.19 | C2/c |
| BPR48A2 | Zn(NO$_3$)$_2$6H$_2$O 0.012 mmol H$_2$BDC 0.012 mmol | DMSO Toluene | 90 | 90 | 90 | 14.5 | 17.04 | 18.02 | Pbca |
| BPR49B1 | Zn(NO$_3$)$_2$6H$_2$O 0.024 mmol H$_2$BDC 0.048 mmol | DMSO Methanol | 90 | 91.172 | 90 | 33.181 | 9.824 | 17.884 | C2/c |
| BPR56E1 | Zn(NO$_3$)$_2$6H$_2$O 0.012 mmol H$_2$BDC 0.024 mmol | DMSO n-Propanol | 90 | 90.096 | 90 | 14.5873 | 14.153 | 17.183 | P2(1)/n |
| BPR68D10 | Zn(NO$_3$)$_2$6H$_2$O 0.0016 mmol H$_3$BTC 0.0064 mmol | DMSO Benzene | 90 | 95.316 | 90 | 10.0627 | 10.17 | 16.413 | P2(1)/c |

-continued

| MOF-n | Ingredients molar ratio M + L | Solvent S | α | β | γ | a | b | c | Space group |
|---|---|---|---|---|---|---|---|---|---|
| BPR69B1 | $Cd(NO_3)_2 4H_2O$ 0.0212 mmol $H_2BDC$ 0.0428 mmol | DMSO | 90 | 98.76 | 90 | 14.16 | 15.72 | 17.66 | Cc |
| BPR73E4 | $Cd(NO_3)_2 4H_2O$ 0.006 mmol $H_2BDC$ 0.003 mmol | DMSO Toluene | 90 | 92.324 | 90 | 8.7231 | 7.0568 | 18.438 | P2(1)/n |
| BPR76D5 | $Zn(NO_3)_2 6H_2O$ 0.0009 mmol $H_2BzPDC$ 0.0036 mmol | DMSO | 90 | 104.17 | 90 | 14.4191 | 6.2599 | 7.0611 | Pc |
| BPR80B5 | $Cd(NO_3)_2 \cdot 4H_2O$ 0.018 mmol $H_2BDC$ 0.036 mmol | DMF | 90 | 115.11 | 90 | 28.049 | 9.184 | 17.837 | C2/c |
| BPR80H5 | $Cd(NO_3)_2 4H_2O$ 0.027 mmol $H_2BDC$ 0.027 mmol | DMF | 90 | 119.06 | 90 | 11.4746 | 6.2151 | 17.268 | P2/c |
| BPR82C6 | $Cd(NO_3)_2 4H_2O$ 0.0068 mmol $H_2BDC$ 0.202 mmol | DMF | 90 | 90 | 90 | 9.7721 | 21.142 | 27.77 | Fdd2 |
| BPR86C3 | $Co(NO_3)_2 6H_2O$ 0.0025 mmol $H_2BDC$ 0.075 mmol | DMF | 90 | 90 | 90 | 18.3449 | 10.031 | 17.983 | Pca2(1) |
| BPR86H6 | $Cd(NO_3)_2 \cdot 6H_2O$ 0.010 mmol $H_2BDC$ 0.010 mmol | DMF | 80.98 | 89.69 | 83.412 | 9.8752 | 10.263 | 15.362 | P-1 |
|  | $Co(NO_3)_2 6H_2O$ | NMP | 106.3 | 107.63 | 107.2 | 7.5308 | 10.942 | 11.025 | P1 |
| BPR95A2 | $Zn(NO_3)_2 6H_2O$ 0.012 mmol $H_2BDC$ 0.012 mmol | NMP | 90 | 102.9 | 90 | 7.4502 | 13.767 | 12.713 | P2(1)/c |
| $CuC_6F_4O_4$ | $Cu(NO_3)_2 \cdot 2.5H_2O$ 0.370 mmol $H_2BDC(OH)_2$ 0.37 mmol | DMF Chlorobenzene | 90 | 98.834 | 90 | 10.9675 | 24.43 | 22.553 | P2(1)/n |
| Fe Formic | $FeCl_2 \cdot 4H_2O$ 0.370 mmol formic acid 0.37 mmol | DMF | 90 | 91.543 | 90 | 11.495 | 9.963 | 14.48 | P2(1)/n |
| Mg Formic | $Mg(NO_3)_2 \cdot 6H_2O$ 0.370 mmol formic acid 0.37 mmol | DMF | 90 | 91.359 | 90 | 11.383 | 9.932 | 14.656 | P2(1)/n |
| $MgC_6H_4O_6$ | $Mg(NO_3)_2 \cdot 6H_2O$ 0.370 mmol $H_2BDC(OH)_2$ 0.37 mmol | DMF | 90 | 96.624 | 90 | 17.245 | 9.943 | 9.273 | C2/c |
| $ZnC_2H_4BDC$ MOF-38 | $ZnCl_2$ 0.44 mmol CBBDC 0.261 mmol | DMF | 90 | 94.714 | 90 | 7.3386 | 16.834 | 12.52 | P2(1)/n |
| MOF-49 | $ZnCl_2$ 0.44 mmol m-BDC 0.261 mmol | DMF $CH_3CN$ | 90 | 93.459 | 90 | 13.509 | 11.984 | 27.039 | P2/c |
| MOF-26 | $Cu(NO_3)_2 \cdot 5H_2O$ 0.084 mmol DCPE 0.085 mmol | DMF | 90 | 95.607 | 90 | 20.8797 | 16.017 | 26.176 | P2(1)/n |
| MOF-112 | $Cu(NO_3)_2 \cdot 2.5H_2O$ 0.084 mmol o-Br-m-BDC 0.085 mmol | DMF Ethanol | 90 | 107.49 | 90 | 29.3241 | 21.297 | 18.069 | C2/c |
| MOF-109 | $Cu(NO_3)_2 \cdot 2.5H_2O$ 0.084 mmol KDB 0.085 mmol | DMF | 90 | 111.98 | 90 | 23.8801 | 16.834 | 18.389 | P2(1)/c |

-continued

| MOF-n | Ingredients molar ratio M + L | Solvent S | α | β | γ | a | b | c | Space group |
|---|---|---|---|---|---|---|---|---|---|
| MOF-111 | Cu(NO$_3$)$_2$·2.5H$_2$O 0.084 mmol o-BrBDC 0.085 mmol | DMF Ethanol | 90 | 102.16 | 90 | 10.6767 | 18.781 | 21.052 | C2/c |
| MOF-110 | Cu(NO$_3$)$_2$·2.5H$_2$O 0.084 mmol thiophene dicarboxylic acid 0.085 mmol | DMF | 90 | 90 | 120 | 20.0652 | 20.065 | 20.747 | R-3/m |
| MOF-107 | Cu(NO$_3$)$_2$·2.5H$_2$O 0.084 mmol thiophene dicarboxylic acid 0.085 mmol | DEF | 104.8 | 97.075 | 95.206 | 11.032 | 18.067 | 18.452 | P-1 |
| MOF-108 | Cu(NO$_3$)$_2$·2.5H$_2$O 0.084 mmol thiophene dicarboxylic acid 0.085 mmol | DBF/ Methanol | 90 | 113.63 | 90 | 15.4747 | 14.514 | 14.032 | C2/c |
| MOF-102 | Cu(NO$_3$)$_2$·2.5H$_2$O 0.084 mmol H$_2$(BDCCl$_2$) 0.085 mmol | DMF | 91.63 | 106.24 | 112.01 | 9.3845 | 10.794 | 10.831 | P-1 |
| Clbdc1 | Cu(NO$_3$)$_2$·2.5H$_2$O 0.084 mmol H$_2$(BDCCl$_2$) 0.085 mmol | DEF | 90 | 105.56 | 90 | 14.911 | 15.622 | 18.413 | P-1 |
| Cu(NMOP) | Cu(NO$_3$)$_2$·2.5H$_2$O 0.084 mmol NBDC 0.085 mmol | DMF | 90 | 102.37 | 90 | 14.9238 | 18.727 | 15.529 | P2(1)/m |
| Tb(BTC) | Tb(NO$_3$)$_3$·5H$_2$O 0.033 mmol H$_3$BTC 0.033 mmol | DMF | 90 | 106.02 | 90 | 18.6986 | 11.368 | 19.721 | |
| Zn$_3$(BTC)$_2$ Honk | ZnCl$_2$ 0.033 mmol H$_3$BTC 0.033 mmol | DMF Ethanol | 90 | 90 | 90 | 26.572 | 26.572 | 26.572 | Fm-3m |
| Zn$_4$O(NDC) | Zn(NO$_3$)$_2$·4H$_2$O 0.066 mmol 14NDC 0.066 mmol | DMF Ethanol | 90 | 90 | 90 | 41.5594 | 18.818 | 17.574 | aba2 |
| CdTDC | Cd(NO$_3$)$_2$·4H$_2$O 0.014 mmol thiophene 0.040 mmol DABCO 0.020 mmol | DMF H$_2$O | 90 | 90 | 90 | 12.173 | 10.485 | 7.33 | Pmma |
| IRMOF-2 | Zn(NO$_3$)$_2$·4H$_2$O 0.160 mmol o-Br-BDC 0.60 mmol | DEF | 90 | 90 | 90 | 25.772 | 25.772 | 25.772 | Fm-3m |
| IRMOF-3 | Zn(NO$_3$)$_2$·4H$_2$O 0.20 mmol H$_2$N-BDC 0.60 mmol | DEF Ethanol | 90 | 90 | 90 | 25.747 | 25.747 | 25.747 | Fm-3m |
| IRMOF-4 | Zn(NO$_3$)$_2$·4H$_2$O 0.11 mmol [C$_3$H$_7$O]$_2$-BDC 0.48 mmol | DEF | 90 | 90 | 90 | 25.849 | 25.849 | 25.849 | Fm-3m |
| IRMOF-5 | Zn(NO$_3$)$_2$·4H$_2$O 0.13 mmol [C$_5$H$_{11}$O]$_2$-BDC 0.50 mmol | DEF | 90 | 90 | 90 | 12.882 | 12.882 | 12.882 | Pm-3m |
| IRMOF-6 | Zn(NO$_3$)$_2$·4H$_2$O 0.20 mmol [C$_2$H$_4$]-BDC 0.60 mmol | DEF | 90 | 90 | 90 | 25.842 | 25.842 | 25.842 | Fm-3m |
| IRMOF-7 | Zn(NO$_3$)$_2$·4H$_2$O 0.07 mmol 1,4NDC 0.20 mmol | DEF | 90 | 90 | 90 | 12.914 | 12.914 | 12.914 | Pm-3m |

-continued

| MOF-n | Ingredients molar ratio M + L | Solvent S | α | β | γ | a | b | c | Space group |
|---|---|---|---|---|---|---|---|---|---|
| IRMOF-8 | Zn(NO$_3$)$_2$·4H$_2$O 0.55 mmol 2,6NDC 0.42 mmol | DEF | 90 | 90 | 90 | 30.092 | 30.092 | 30.092 | Fm-3m |
| IRMOF-9 | Zn(NO$_3$)$_2$·4H$_2$O 0.05 mmol BPDC 0.42 mmol | DEF | 90 | 90 | 90 | 17.147 | 23.322 | 25.255 | Pnnm |
| IRMOF-10 | Zn(NO$_3$)$_2$·4H$_2$O 0.02 mmol BPDC 0.012 mmol | DEF | 90 | 90 | 90 | 34.281 | 34.281 | 34.281 | Fm-3m |
| IRMOF-11 | Zn(NO$_3$)$_2$·4H$_2$O 0.05 mmol HPDC 0.20 mmol | DEF | 90 | 90 | 90 | 24.822 | 24.822 | 56.734 | R-3m |
| IRMOF-12 | Zn(NO$_3$)$_2$·4H$_2$O 0.017 mmol HPDC 0.12 mmol | DEF | 90 | 90 | 90 | 34.281 | 34.281 | 34.281 | Fm-3m |
| IRMOF-13 | Zn(NO$_3$)$_2$·4H$_2$O 0.048 mmol PDC 0.31 mmol | DEF | 90 | 90 | 90 | 24.822 | 24.822 | 56.734 | R-3m |
| IRMOF-14 | Zn(NO$_3$)$_2$·4H$_2$O 0.17 mmol PDC 0.12 mmol | DEF | 90 | 90 | 90 | 34.381 | 34.381 | 34.381 | Fm-3m |
| IRMOF-15 | Zn(NO$_3$)$_2$·4H$_2$O 0.063 mmol TPDC 0.025 mmol | DEF | 90 | 90 | 90 | 21.459 | 21.459 | 21.459 | Im-3m |
| IRMOF-16 | Zn(NO$_3$)$_2$·4H$_2$O 0.0126 mmol TPDC 0.05 mmol | DEF NMP | 90 | 90 | 90 | 21.49 | 21.49 | 21.49 | Pm-3m |

ADC Acetylenedicarboxylic acid
NDC Naphthalenedicarboxylic acid
BDC Benzenedicarboxylic acid
ATC Adamantanetetracarboxylic acid
BTC Benzenetricarboxylic acid
BTB Benzenetribenzoic acid
MTB Methanetetrabenzoic acid
ATB Adamantanetetrabenzoic acid
ADB Adamantanedibenzoic acid Further MOFs are MOF-177, MOF-178, MOF-74, MOF-235, MOF-236, MOF-69 to 80, MOF-501, MOF-502, which are described in the literature.

In particular preference is given to a porous metal-organic framework material in which Zn, Al, Ni or Cu is present as metal ion and the at least bidentate organic compound is terephthalic acid, isophthalic acid, 2,6-naphthalenedicarboxylic acid or 1,3,5-benzenetricarboxylic acid.

In addition to the conventional method for producing the MOFs, as is described, for example, in U.S. Pat. No. 5,648,508, they can also be produced in an electrochemical method. In this respect, reference is made to DE-A 103 55 087 and also WO-A 2005/049892. The MOFs produced in this manner exhibit particularly good properties in connection with adsorption and desorption of chemical substances, in particular gases. They are thus different from those which are produced conventionally, even when they are formed from the same organic and metal-ion constituents, and are therefore to be considered novel framework materials. In the context of the present invention, electrochemically produced MOFs are particularly preferred.

Accordingly, the electrochemical production relates to a crystalline porous metal-organic framework material comprising at least one, at least bidentate, organic compound bound by coordination to at least one metal ion, which is produced in a reaction medium comprising the at least one bidentate organic compound at least one metal ion by oxidation of at least one anode comprising the corresponding metal.

The term "electrochemical production" designates a production method in which the formation of at least one reaction product is associated with the migration of electric charges or the occurrence of electric potentials.

The term "at least one metal ion", as used in connection with the electrochemical production, designates embodiments according to which at least one ion of a metal ion or at least one ion of a first metal and at least one ion of at least one second metal different from the first metal are provided by anodic oxidation.

Accordingly, the electrochemical production relates to embodiments in which at least one ion of at least one metal is provided by anodic oxidation and at least one ion of at least one metal is provided by a metal salt, the at least one metal in the metal salt and the at least one metal which is provided as metal ion via anodic oxidation being able to be identical or different from one another. Therefore, the present invention, in relation to electrochemically produced MOFs comprises, for example, an embodiment according to which the reaction medium comprises one or more different salts of a metal and the metal ion present in this salt or in these salts is additionally provided by anodic oxidation of at least one anode comprising this metal. Likewise, the reaction medium can comprise one or more different salts of at least one metal and at least one metal different from these metals can be provided via anodic oxidation as metal ion in the reaction medium.

According to a preferred embodiment of the present invention in connection with the electrochemical production, the at least one metal ion is provided by anodic oxidation of at least one anode comprising this at least one metal, no further metal being provided via a metal salt.

The term "metal", as used in the context of the present invention in connection with the electrochemical production of MOFs, comprises all elements of the Periodic Table of the Elements which can be provided via anodic oxidation in the electrochemical method in a reaction medium and are able with at least one at least bidentate organic compound to form at least one metal-organic porous framework material.

Independently of its production, the resultant MOF is produced in powder or crystalline form. This is preferably used as such in the inventive suspension. In this case the metal-organic framework material acts as sorbent. Furthermore, other sorbents can also be used in the suspension. In principle, the metal-organic framework material can also be converted into a shaped body and this can be used in the inventive suspension.

The present invention further relates to the use of the inventive suspension for odor reduction.

The invention will be described in more detail hereinafter by the following examples.

EXAMPLES

Example 1

On the basis of an odor test, the action of an inventive suspension having various metal-organic framework materials is investigated with respect to the reduction of odor due to odor substances from cigarette smoke. A suspension of β-cyclodextrin, and also pure water, are used as comparison.

The following samples are used:
Sample 1: 0.5% by weight of β-cyclodextrin in water,
Sample 2: 0.5% by weight of MOF-5 in water (Zn with terephthalic acid),
Sample 3: 0.5% by weight of IR-MOF-8 in water (Zn with 2,6-naphthalenedicarboxylic acid),
Sample 4: 0.5% by weight of copper framework material produced electrochemically according to Example 2 of WO-A 2005/049892 and also water.

The apparatus used is a 10 l vessel having two closeable openings situated at opposite points. The test fabric used is cotton body Lg. No, 286. In addition, a cigarette of the brand Gauloises Blondes, blue packet (10 mg tar, 0.8 mg nicotine) is used. For preparation, the test fabric is suspended in the apparatus. At one opening, a cigarette is mounted in such a manner that smoke can be drawn through the filter of the cigarette into the vessel. At the other opening, a vacuum is applied in order to be able to draw the smoke into the vessel. Vacuum is controlled manually via a T piece in such a manner that the cigarette burns as uniformly as possible with 2 minutes up to the start of the line. Thereafter the vacuum is to be taken rapidly from the apparatus and the apparatus is to be closed on both sides. The test fabric is then left for 2 hours in the apparatus, cut to 6×6 cm and if appropriate placed for storage in a closed plastic flask. From a distance of approximately 30 cm, the test fabric is brought into contact by spraying samples 1 to 4 and also water by two spray bursts (approximately 2.5 ml) using a commercially conventional pressure-pump atomizer, in such a manner that the entire surface of the test fabric is wetted. Thereafter, the test fabrics are dried at room temperature for 1 hour, hanging freely. The test fabrics are rated with respect to their odor immediately in the moist state (Table A), and after 6 hours in the dry state (Table B).

Assessment Score 1=without odor
10=strong cigarette odor

TABLE A

| Assessor | Sample 1 | Sample 2 | Sample 3 | Sample 4 | Water |
|---|---|---|---|---|---|
| A | 4 | 8 | 5 | 5 | 10 |
| B | 3 | 10 | 6 | 7 | 10 |
| C | 5 | 7 | 4 | 6 | 10 |
| D | 4 | 7 | 7 | 4 | 9 |
| E | 4 | 8 | 4 | 4 | 10 |
| F | 5 | 6 | 4 | 4 | 10 |
| G | 3 | 9 | 5 | 5 | 10 |
| H | 4 | 8 | 5 | 4 | 10 |
| Average | 4.0 | 7.9 | 5 | 4.9 | 9.9 |

TABLE B

| Assessor | Sample 1 | Sample 2 | Sample 3 | Sample 4 | Water |
|---|---|---|---|---|---|
| A | 6 | 8 | 3 | 4 | 10 |
| B | 5 | 7 | 4 | 5 | 10 |
| C | 10 | 4 | 5 | 5 | 10 |
| D | 5 | 5 | 3 | 3 | 9 |
| E | 6 | 8 | 3 | 2 | 10 |
| F | 6 | 9 | 1 | 3 | 10 |
| G | 5 | 10 | 2 | 1 | 10 |
| H | 5 | 7 | 1 | 2 | 10 |
| Average | 6.0 | 7.4 | 2.8 | 3.5 | 9.9 |

Example 2

Samples Tested:
water, samples 1 to 3 according to example 1
Reagents:
cotton twill Lg. No. 286
cigarette (Gauloises Blondes, blue packet, 10 mg tar, 0.8 mg nicotine)
Preparation:

The test fabrics are suspended in the apparatus described in example 1. At one opening, a cigarette is mounted in such a manner that smoke can be drawn through the filter of the cigarette into the vessel. At the other opening, a vacuum is applied in order to be able to draw the smoke into the vessel. Vacuum is controlled manually via a T piece in such a manner that the cigarette burns as uniformly as possible within 2 minutes up to the start of the line. Thereafter the vacuum is to be taken as rapidly as possible from the apparatus and the apparatus is to be closed on both sides. The test fabrics are then left for two hours in the apparatus, cut to 6×6 cm, and if appropriate placed for storage in a closed plastic bottle.
Procedure:

The test fabrics are attached to a filter paper which is suspended vertically on a non-absorbent wall.

From a distance of 30 cm, per fabric and per sample under test, 2 spray bursts (approximately 2.5 ml) are applied by the atomizer in such a manner that the entire surface of the test fabric is wetted. Thereafter the test fabrics are dried at room temperature for 30 min, hanging freely. The test fabrics are rated with respect to their odor. The result is presented in the table hereinafter.

Assessment score 1=without odor
   10=strong cigarette odor

| Assessor | Smoker | Untreated | Water | Sample 1 | Sample 2 | Sample 3 |
|---|---|---|---|---|---|---|
| A | No | 7 | 7 | 8 | 6 | 5 |
| B | Yes | 7 | 8 | 6 | 5 | 5 |
| C | No | 7 | 8 | 7 | 6 | 6 |
| D | No | 9 | 8 | 6 | 8 | 4 |
| E | No | 9 | 8 | 8 | 8 | 7 |
| F | No | 8 | 7 | 5 | 7 | 5 |
| G | Yes | 9 | 6 | 9 | 3 | 8 |
| H | Yes | 8 | 6 | 5 | 5 | 7 |
| I | Yes | 9 | 7 | 4 | 5 | 6 |
| J | No | 10 | 6 | 3 | 2 | 2 |
| Mean | | 9.3 | 8.1 | 7.1 | 6.6 | 6.7 |

The invention claimed is:

1. A method for odor reduction, comprising contacting a gas comprising the odor, or an odor adhering to the surface of an article or to an organism with a suspension for odor reduction comprising:
   a porous metal-organic framework material in a liquid, the framework material comprising
   at least one, at least bidentate, organic compound bound by coordination to at least one metal ion, wherein
   the concentration of the framework material is in the range from 0.01 to 2.5% by weight based on the total weight of the suspension,
   the liquid contains water or is water, and
   the odor is caused by tobacco smoke.

2. The method of claim 1, wherein the framework material comprises Zn, Al, Ni or Cu as the metal ion and the at least bidentate organic compound is terephthalic acid, isophthalic acid, 2,6naphthalenedicarboxylic acid or 1,3,5-benzenetricarboxylic acid.

3. The method of claim 1, wherein the suspension is contained in an atomizer.

4. The method of claim 1, wherein the gas is air.

5. The method of claim 1, wherein the odor is caused by at least one odor substance and wherein the odor substance has a vapor pressure of greater than 0.001 kpa at 20° C.

6. The method of claim 1, wherein the odor is caused by at least one odor substance and wherein the odor substance has a vapor pressure of great than 0.001 kPa at 20° C.

7. The method of claim 1, wherein the metal-organic framework material comprises micropores.

8. The method of claim 1, wherein the metal-organic framework material comprises micropores and/or mesopores.

9. The method of claim 1, wherein the metal-organic framework material comprises pores with a size of 0.2 nm to 30 nm.

* * * * *